US012742197B2

(12) United States Patent
Heindl et al.

(10) Patent No.: US 12,742,197 B2
(45) Date of Patent: Sep. 22, 2026

(54) DETECTION OF TARGET NUCLEIC ACID BY SOLID-PHASE MOLOGRAPHY

(71) Applicant: Roche Molecular Systems, Inc., Pleasanton, CA (US)

(72) Inventors: Dieter Heindl, Munich (DE); Igor Kozlov, Danville, CA (US); Nikolaus-Peter Stengele, Pleiskirchen (DE); Alison Tsan, Danville, CA (US); Volker Gatterdam, Nuestal (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 1297 days.

(21) Appl. No.: 17/633,359

(22) PCT Filed: Dec. 19, 2019

(86) PCT No.: PCT/EP2019/086145
§ 371 (c)(1),
(2) Date: Feb. 7, 2022

(87) PCT Pub. No.: WO2020/127620
PCT Pub. Date: Jun. 25, 2020

(65) Prior Publication Data

US 2022/0298555 A1 Sep. 22, 2022

Related U.S. Application Data

(60) Provisional application No. 62/782,867, filed on Dec. 20, 2018.

(51) Int. Cl.
*C12Q 1/6825* (2018.01)
*C12Q 1/6853* (2018.01)
*C12Q 1/686* (2018.01)

(52) U.S. Cl.
CPC ......... *C12Q 1/6825* (2013.01); *C12Q 1/6853* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 9,611,506 B2 | 4/2017 | Engel | |
| 9,637,791 B2 | 5/2017 | Gupta | |
| 2010/0041040 A1* | 2/2010 | Babiel | C12Q 1/6888 435/6.1 |
| 2014/0272955 A1 | 9/2014 | Gupta | |
| 2016/0139115 A1 | 5/2016 | Fattinger | |
| 2018/0073064 A1 | 3/2018 | Kozlov et al. | |

FOREIGN PATENT DOCUMENTS

| | | | |
|---|---|---|---|
| CA | 2562390 | A1 | 10/2005 |
| CA | 2961417 | A1 | 3/2016 |
| CN | 1737165 | A | 2/2006 |
| CN | 1961081 | A | 5/2007 |
| CN | 105899676 | A | 8/2016 |
| CN | 106687597 | A | 5/2017 |
| EP | 2052086 | A1 | 4/2009 |
| WO | 2013022807 | A1 | 2/2013 |
| WO | 2014104818 | A1 | 7/2014 |

OTHER PUBLICATIONS

Johnson-Buck, Kinetic fingerprinting to identify and count single nucleic acids, Nat Biotechnol, 33(7): 730-732, 2015. (Year: 2015).*
Chinese Office Action issued Jun. 18, 2024 in Appln. No. 201980084644. 4, 7 pages.
Fattinger, C., "Focal Molography: Coherent Microscopic Detection of Biomolecular Interaction", Physical Review X 4, 031024 (2014).
Gatterdam, V. et al., "Focal molography is a new method for the in situ analysis of molecular interactions in biological samples", Nature Nanotechnology, vol. 12, No. 11, Sep. 25, 2017, pp. 1089-1095.
International Search Report and Written Opinion for PCT/EP2019/083389, mailed Feb. 17, 2020.

* cited by examiner

*Primary Examiner* — Carolyn L Greene
(74) *Attorney, Agent, or Firm* — Daniel E. Agnew

(57) ABSTRACT

The present invention describes methods for performing real-time PCR for detection and quantitation of target nucleic acids using tagged oligonucleotide probes and solid-phase molography.

11 Claims, 4 Drawing Sheets

Specification includes a Sequence Listing.

```
                              SEQUENCE LISTING

<160> NUMBER OF SEQ ID NOS: 4

<210> SEQ ID NO 1
<211> LENGTH: 49
<212> TYPE: DNA
<213> ORGANISM: Artificial Sequence
<220> FEATURE:
<223> OTHER INFORMATION: HIV-1 LTR tag 3 probe

<400> SEQUENCE: 1

cacacattgg caccgccgtc ttctctagca gtggcgcccg aacagggac                49


<210> SEQ ID NO 2
<211> LENGTH: 38
<212> TYPE: DNA
<213> ORGANISM: Artificial Sequence
<220> FEATURE:
<223> OTHER INFORMATION: Moligo tag 3 oligonucleotide

<400> SEQUENCE: 2

tttttttttt ttagagaaga cggcggtgcc aatgtgtg                            38


<210> SEQ ID NO 3
<211> LENGTH: 22
<212> TYPE: DNA
<213> ORGANISM: Artificial Sequence
<220> FEATURE:
<223> OTHER INFORMATION: AT-MOLO-3 oligonucleotide

<400> SEQUENCE: 3

cacacattgg caccgccgtc tt                                             22


<210> SEQ ID NO 4
<211> LENGTH: 100
<212> TYPE: DNA
<213> ORGANISM: Artificial Sequence
<220> FEATURE:
<223> OTHER INFORMATION: HIV-LTR-moligo-100 oligonucleotide

<400> SEQUENCE: 4

ttgcatgaga atagtaacgt attgtgtaaa gcaggatata gagtaattgc ccagttgttc     60

caaatcgata ttgcagagaa gacggcggtg ccaatgtgtg                          100
```

DETECTION OF TARGET NUCLEIC ACID BY SOLID-PHASE MOLOGRAPHY

CROSS REFERENCE TO RELATED APPLICATIONS

This application is a U.S. national stage filing under 35 U.S.C. § 371 of International Application No. PCT/EP2019/086145, filed Dec. 19, 2019, entitled "DETECTION OF TARGET NUCLEIC ACID BY SOLID-PHASE MOLOGRAPHY", which claims the benefit of priority to U.S. Provisional Application No. 62/782,867, filed on Dec. 20, 2018, the disclosure of each of which is incorporated herein by reference in its entirety.

FIELD OF THE INVENTION

The present invention relates to methods for polymerase chain reaction (PCR) particularly to methods for performing multiplexed PCR and detection of target nucleic acids by a solid-phase biosensor

REFERENCE TO SEQUENCE LISTING

This application contains a Sequence Listing submitted as an electronic text file named "P34923-WO PCT fling sequence listing", having a size in bytes of 1,200 bytes, and created on Nov. 17, 2019.

BACKGROUND OF THE INVENTION

The polymerase chain reaction (PCR) has become a ubiquitous tool of biomedical research, disease monitoring and diagnostics. Amplification of nucleic acid sequences by PCR is described in U.S. Pat. Nos. 4,683,195, 4,683,202, and 4,965,188. PCR is now well known in the art and has been described extensively in the scientific literature. See PCR Applications, ((1999) Innis et al., eds., Academic Press, San Diego), PCR Strategies, ((1995) Innis et al., eds., Academic Press, San Diego); PCR Protocols, ((1990) Innis et al., eds., Academic Press, San Diego), and PCR Technology, ((1989) Erlich, ed., Stockton Press, New York). A "real-time" PCR assay is able to simultaneously amplify and detect and quantify the starting amount of the target sequence. The basic TaqMan® real-time PCR assay using the 5'-to-3' nuclease activity of the DNA polymerase is described in Holland et al., (1991) Proc. Natl. Acad. Sci. 88: 7276-7280 and U.S. Pat. No. 5,210,015. The real-time PCR without the nuclease activity (a nuclease-free assay) has been described in a U.S. application Ser. No. 12/330,694 filed on Dec. 9, 2008. The use of fluorescent probes in real-time PCR is described in U.S. Pat. No. 5,538,848.

With the majority of current methods, the ability to multiplex an assay is limited by the detection instruments. Specifically, the use of multiple probes in the same reaction requires the use of distinct fluorescent labels. To simultaneously detect multiple probes, an instrument must be able to discriminate among the light signals emitted by each probe. The majority of current technologies on the market do not permit detection of more than four to seven separate wavelengths in the same reaction vessel. Therefore, using one uniquely-labeled probe per target, no more than four to seven separate targets can be detected in the same vessel. In practice, at least one target is usually a control nucleic acid. Accordingly, in practice, no more than three to six experimental targets can be detected in the same tube. The use of fluorescent dyes is also limited due to the spectral width where only about six or seven dyes can be fit within the visible spectrum without significant overlap interference. Thus the ability to multiplex an assay will not keep pace with the clinical needs, unless radical changes in the amplification and detection strategy are made.

Many methods for detection of target nucleic acids are known. Currently available homogeneous assays for nucleic acid detection include the TaqMan®, Ampliflour®, dye-binding, allele-selective kinetic PCR and Scorpion® primer assays. As stated above, these assay procedures are not readily multiplexed due to the requirement for a different dye for each target nucleic acid to be detected, and thus are limited in their potential for improvement. To overcome such limitations, several recent studies have disclosed the use of oligonucleotide probes containing a cleavable "tag" portion which can be readily separated and detected (e.g. see Chenna et al, U.S. Patent Application Publication No. 2005/0053939; Van Den Boom, U.S. Pat. No. 8,133,701). More recently, improved methods to perform multiplexed nucleic acid target identification by using structure based oligonucleotide probe cleavage have been described in U.S. Patent Application Publication No. 2014/0272955, U.S. 2015/0176075, and U.S. 2015/0376681, all incorporated by reference herein. Further methods to detect target nucleic acid sequence from DNA or a mixture of nucleic acid by the use of a combination of "Probing and Tagging Oligonucleotide" (PTO) and "Capturing and Templating Oligonucleotide" (CTO) in a so-called PTO Cleavage and Extension assay have been described by Chun et al. in U.S. Pat. No. 8,809,239. However, the need still exists for an accurate method to perform high throughput multiplex detection of target nucleic acids, especially one that is not limited by the use of fluorescent dyes or labels (i.e. label-free multiplex detection of target nucleic acids).

Focal molography has been described recently as an analytical method that visualizes specific biomolecular interactions in real time (see Fattinger C., *Physical Review X* 4, 031024, 2014; Fattinger C., U.S. 2016/0139115; and Gatterdam, V. et al., *Nature Nanotechnology* 12, 1089-1095, 2017, the disclosures of which are incorporated herein by reference in their entireties). Focal molography transduces affinity modulation on the sensor surface into refractive index modulation caused by target molecules that are bound to a precisely assembled nanopattern of molecular recognition sites, termed the "mologram". The mologram is designed so that laser light is scattered at specifically bound molecules, generating a strong signal in the focus of the mologram via constructive interference, while scattering at non-specifically bound molecules would not contribute to the effect. The mologram can be presented on a chip by near-field reactive immersion lithography on a light-sensitive monolithic graft copolymer layer. Selective, sensitive and label-free detection of biomolecules that bind to recognition sites of the mologram can be demonstrated.

SUMMARY OF THE INVENTION

The present invention provides for novel methods for nucleic acid sequence detection, particularly the amplification and detection of multiple target nucleic acids using a real-time PCR assay and solid-phase focal molography. The methods are performed by the use of oligonucleotide probes each one comprising an annealing portion and a tag portion, referred as "tagged probes", wherein the tag portion comprises a nucleotide sequence non-complementary to the target nucleic acid sequence, wherein the annealing portion comprises a nucleotide sequence at least partially complementary to the target nucleic acid sequence and hybridizes to a region of the subsequence of the target nucleic acid. The methods are also performed by the use of oligonucleotides that are attached on molography chips, termed "moligos", each moligo comprising an annealing portion that comprises a nucleotide sequence complementary to the tag portion of one of the oligonucleotide probe, and an extension portion comprising a nucleotide sequence that is non-complementary to the target nucleic acid sequence or to the tag portion.

Therefore, in one embodiment, the present invention relates to a method for amplification and detection of a target nucleic acid in a sample comprising the steps of contacting said sample containing said target nucleic acid in a single reaction vessel with one pair of oligonucleotide primers, each oligonucleotide primer capable of hybridizing to opposite strands of a subsequence of said target nucleic acid; a tagged probe comprising an oligonucleotide sequence that comprises an annealing portion and a tag portion, wherein the tag portion comprises a nucleotide sequence non-complementary to the target nucleic acid sequence, wherein the annealing portion comprises a nucleotide sequence at least partially complementary to the target nucleic acid sequence and hybridizes to a region of said subsequence of said target nucleic acid that is bounded by said pair of oligonucleotide primers; amplifying said target nucleic acid by PCR using a nucleic acid polymerase having 5' to 3' nuclease activity such that during an extension step of each PCR cycle, the nuclease activity of the polymerase allows cleavage and separation of the tag portion from the annealing portion of the tagged probe; hybridizing the cleaved tag portion from the tagged probe with a moligo template comprising an oligonucleotide sequence that comprises an annealing portion comprising a nucleotide sequence complementary to the tag portion of the tagged probe, and an extension portion comprising a nucleotide sequence that is non-complementary to the target nucleic acid sequence or to the tag portion of the tagged probe to form a partial duplex molecule, wherein said moligo template is attached on a solid phase chip; reacting the partial duplex molecule with a nucleic acid polymerase to extend the cleaved tag portion into the extension portion of the moligo template; measuring the extension by molography wherein an increase in a molographic signal between the hybridization step and extension step represents detection of the presence of the target nucleic acid; wherein all steps are performed in the absence of a label. In one particular embodiment, the length of the moligo template is longer than the length of the tagged probe by at least 10 nucleotides. In other embodiments, the length of the moligo is longer than the length of the tagged probe by at least, 20 nucleotides, or 30 nucleotides, or 40 nucleotides, or 50 nucleotides. In certain embodiments, the length of the moligo template is longer than the length of the tag portion of the tagged probe by at least 10 nucleotides. In other embodiments, the length of the moligo is longer than the length of the tag portion of the tagged probe by at least, 20 nucleotides, or 30 nucleotides, or 40 nucleotides, or 50 nucleotides.

DETAILED DESCRIPTION OF THE INVENTION

Definitions

Figure 1:
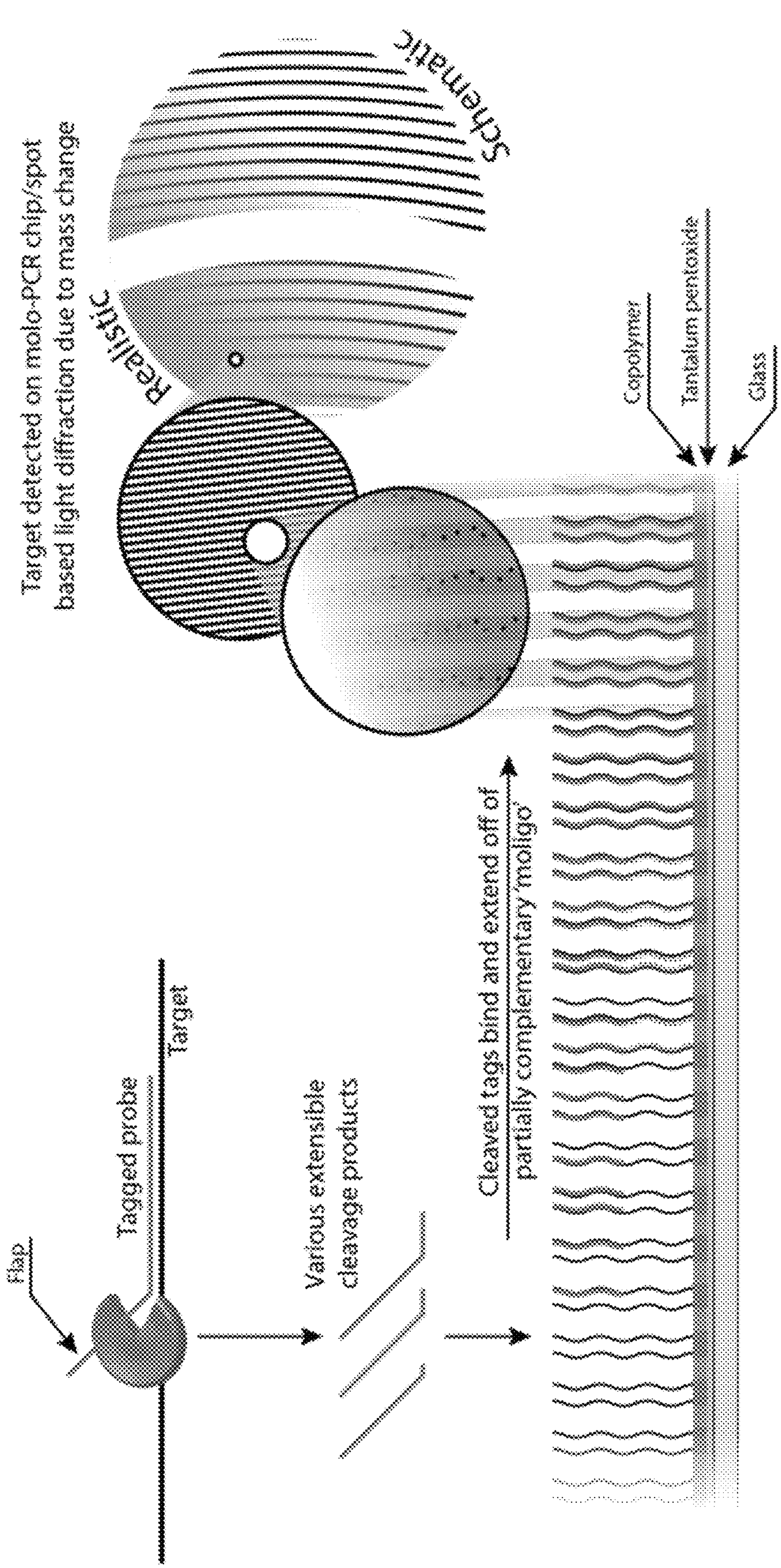
FIG. 1 is a graphical description of the methods of the invention.

The term "sample" as used herein includes a specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "target" or "target nucleic acid" as used herein are intended to mean any molecule whose presence is to be detected or measured or whose function, interactions or properties are to be studied. For example, a target may be a biomolecule, such as a nucleic acid molecule, which is capable of binding with or otherwise coming in contact with an oligonucleotide probe. The terms "nucleic acid" and "nucleic acid molecule" may be used interchangeably throughout the disclosure. The terms refer to oligonucleotides, oligos, polynucleotides, deoxyribo-nucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/nonnaturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have either a known or unknown sequence or structure.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a target nucleic acid template and facilitates the detection of an oligonucleotide probe. In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. Primers can be of a variety of lengths and are often less than 50 nucleotides in length, for example 12-25 nucleotides, in length. The length and sequences of primers for use in PCR can be designed based on principles known to those of skill in the art.

The term "oligonucleotide probe" as used herein refers to a polynucleotide sequence capable of hybridizing or annealing to a target nucleic acid of interest and allows for the specific detection of the target nucleic acid.

A "label" or "label molecule" is a molecule that confers a detectable signal. The detectable signal can be colorimetric, fluorescent or luminescent, for example. Conversely, "label-free" refers to the absence of a molecule that confers a detectable signal. For the purposes of the present invention, an affinity tag that does not by itself confer a detectable signal is not a label and assays that employ an affinity tag that does not by itself confer a detectable signal are considered label-free assays.

A "mismatched nucleotide" or a "mismatch" refers to a nucleotide that is not complementary to the target sequence at that position or positions. An oligonucleotide probe may have at least one mismatch, but can also have 2, 3, 4, 5, 6 or 7 or more mismatched nucleotides.

The term "polymorphism" as used herein refers to an allelic variant. Polymorphisms can include single nucleotide polymorphisms (SNP's) as well as simple sequence length polymorphisms. A polymorphism can be due to one or more nucleotide substitutions at one allele in comparison to another allele or can be due to an insertion or deletion, duplication, inversion and other alterations known to the art.

The term "modification" as used herein refers to alterations of the oligonucleotide probe at the molecular level (e.g., base moiety, sugar moiety or phosphate backbone). Nucleoside modifications include, but are not limited to, the introduction of cleavage blockers or cleavage inducers, the introduction of minor groove binders, isotopic enrichment, isotopic depletion, the introduction of deuterium, and halogen modifications. Nucleoside modifications may also include moieties that increase the stringency of hybridization or increase the melting temperature of the oligonucleotide probe. For example, a nucleotide molecule may be modified with an extra bridge connecting the 2' and 4' carbons resulting in locked nucleic acid (LNA) nucleotide that is resistant to cleavage by a nuclease (as described in Imanishi et al., U.S. Pat. No. 6,268,490 and in Wengel et al., U.S. Pat. No. 6,794,499, both of which are incorporated herein by reference in their entireties). The compositions of the tag portion of the oligonucleotide probe and of the quenching oligonucleotide molecule are only restricted by their ability to form stable duplexes. These oligonucleotides can therefore comprise of DNA, L-DNA, RNA, L-RNA, LNA, L-LNA, PNA (peptide nucleic acid, as described in Nielsen et al., U.S. Pat. No. 5,539,082), BNA (bridged nucleic acid, for example, 2',4'-BNA(NC) [2'-O,4'-C-aminomethylene bridged nucleic acid] as described in Rahman et al., J. Am. Chem. Soc. 2008; 130(14): 4886-96), L-BNA etc. (where the "L-XXX" refers to the L-enantiomer of the sugar unit of the nucleic acids) or any other known variations and modifications on the nucleotide bases, sugars, or phosphodiester backbones.

Other examples of nucleoside modifications include various 2' substitutions such as halo, alkoxy and allyloxy groups that are introduced in the sugar moiety of oligonucleotides. Evidence has been presented that 2'-substituted-2'-deoxyadenosine polynucleotides resemble double-stranded RNA rather than DNA. Ikehara et al., (Nucleic Acids Res., 1978, 5, 3315) have shown that a 2'-fluro substituent in poly A, poly I, or poly C duplexed to its complement is significantly more stable than the ribonucleotide or deoxyribonucleotide poly duplex as determined by standard melting assays. Inoue et al., (Nucleic Acids Res., 1987, 15, 6131) have described the synthesis of mixed oligonucleotide sequences containing 2'-OMe (O-Methyl) substituents on every nucleic nucleotide. The mixed 2'-OMe-substituted oligonucleotide hybridized to its RNA complement as strongly as the RNA-RNA duplex which is significantly stronger than the same sequence RNA-DNA heteroduplex. Therefore, examples of substitutions at the 2' position of the sugar include F, CN, $CF_3$, $OCF_3$, OMe, OCN, O-alkyl, S-alkyl, SMe, $SO_2Me$, $ONO_2$, $NO_2$, $NH_3$, $NH_2$, NH-alkyl, $OCH_3{=}CH_2$ and OCCH.

The term "specific" or "specificity" in reference to the binding of one molecule to another molecule, such as a probe for a target polynucleotide, refers to the recognition, contact, and formation of a stable complex between the two molecules, together with substantially less recognition, contact, or complex formation of that molecule with other molecules. As used herein, the term "anneal" refers to the formation of a stable complex between two molecules. A probe is "capable of annealing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, 95% or 99%, and most preferably 100%. For the purpose of determining sequence identity of a DNA sequence and a RNA sequence, U and T often are considered the same nucleotide. For example, a probe comprising the sequence ATCAGC is capable of hybridizing to a target RNA sequence comprising the sequence GCUGAU.

The term "cleavage agent" as used herein refers to any means that is capable of cleaving an oligonucleotide probe to yield fragments, including but not limited to enzymes. For methods wherein amplification does not occur, the cleavage agent may serve solely to cleave, degrade or otherwise separate the second portion of the oligonucleotide probe or fragments thereof. The cleavage agent may be an enzyme. The cleavage agent may be natural, synthetic, unmodified or modified.

For methods wherein amplification occurs, the cleavage agent is preferably an enzyme that possesses synthetic (or polymerization) activity and nuclease activity. Such an enzyme is often a nucleic acid amplification enzyme. An example of a nucleic acid amplification enzyme is a nucleic acid polymerase enzyme such as *Thermus aquaticus* (Taq) DNA polymerase (TagMan®) or *E. coli* DNA polymerase I. The enzyme may be naturally occurring, unmodified or modified.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable DNA polymerase" refers to a DNA polymerase that is stable (i.e., resists breakdown or denaturation) and retains sufficient catalytic activity when subjected to elevated temperatures for selected periods of time. For example, a thermostable DNA polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, AZO5R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not. Some enzymes that have 5' to 3' nuclease activity are 5' to 3' exonucleases. Examples of such 5' to 3' exonucleases include: Exonuclease from *B. subtilis*, Phosphodiesterase from spleen, Lambda exonuclease, Exo-nuclease II from yeast, Exonuclease V from yeast, and Exonuclease from *Neurospora crassa*.

The term "propanediol" or "propanediol spacer" refers to 1,3-Propanediol and is synonymous with Propane-1,3-diol, 1,3-Dihydroxypropane, and Trimethylene glycol. The term "HEG" or "HEG spacer" refers to hexaethylene glycol, which is synonymous with 3,6,9,12,15-Pentaoxaheptadecane-1,17-diol.

Various aspects of the present invention are based on a special property of nucleic acid polymerases. Nucleic acid polymerases can possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur efficiently, an upstream oligonucleotide must also be annealed to the same larger polynucleotide.

The detection of a target nucleic acid utilizing the 5' to 3' nuclease activity can be performed by a "TagMan®" or "5'-nuclease assay", as described in U.S. Pat. Nos. 5,210,015; 5,487,972; and 5,804,375; and Holland et al., 1988, Proc. Natl. Acad. Sci. USA 88: 7276-7280, all incorporated by reference herein. In the TaqMan® assay, labeled detection probes that hybridize within the amplified region are present during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

A 5' nuclease assay for the detection of a target nucleic acid can employ any polymerase that has a 5' to 3' exonuclease activity. Thus, in some embodiments, the polymerases with 5'-nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*, as well as chimeric forms thereof For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, *Thermus* species sps17 (sps17), and *Thermus* species Z05 (e.g., described in U.S. Pat. Nos. 5,405,774; 5,352,600; 5,079,352; 4,889,818; 5,466,591; 5,618,711; 5,674,738, and 5,795,762. *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/US91/07035 with Publication No. WO 92/06200. The sequence of *Thermatoga neapolitana* may be found in International Patent Publication No. WO 97/09451.

In the 5' nuclease assay, the amplification detection is typically concurrent with amplification (i.e., "real-time"). In some embodiments the amplification detection is quantitative, and the amplification detection is real-time. In some embodiments, the amplification detection is qualitative (e.g., end-point detection of the presence or absence of a target nucleic acid). In some embodiments, the amplification detection is subsequent to amplification. In some embodiments, the amplification detection is qualitative, and the amplification detection is subsequent to amplification.

In the present invention, real-time PCR amplification and detection of two or more target nucleic acid in a single reaction vessel (e.g. tube, well) are performed using oligonucleotide probes, referred as tagged probes, each comprising two distinct portions. The first portion is an annealing portion and comprises a sequence that is at least partially complementary to a target nucleic acid sequence such that it is capable of being hybridized with the target sequence. The second portion of the oligonucleotide probe (i.e. the tagged probe) is referred as a tag portion. In one embodiment, the tag portion is attached to the 5' terminus of the annealing portion. In another embodiment, the tag portion is attached to the 3' terminus of the annealing portion. In another embodiment, the tag portion is attached anywhere between the 5' terminus and the 3' terminus of the annealing portion via a linker. The tag portion may comprise a nucleotide sequence that is not complementary to the target nucleic acid sequence and forms a "flap" region that is not capable of binding to the target nucleic acid (see FIG. 1 for a graphical representation of a 5' flap probe). The annealing and tag portions of the tagged probe may optionally be separated by a non-nucleotide "linker". This linker can be comprised of carbon, carbon and oxygen, carbon and nitrogen, or any combination of these and can be of any length. Furthermore, the linker can be comprised of a linear moiety or a cyclic moiety. The linker may be derived from a single unit or from multiple identical or different units separated by phosphate linkages. The purpose of the linker is to create a region at the junction of the annealing and tag portions of the tagged probe. When the tag portion is separated from the annealing portion, the linker may also prevent the tag portion from being extended by a nucleic acid polymerase. Alternatively, another modification on the separated tag portion renders it non-extendible by the nucleic acid polymerase.

The general principle of using the tagged probe to perform real-time PCR amplification and detection of target nucleic acid in a 5' nuclease assay is described below. First, a sample suspected of containing the target nucleic acid is provided. The sample is then contacted inside a single reaction vessel (e.g. a single test tube or a single well in a multi-well microplate) with PCR reagents that contain both the oligonucleotide primers capable of generating amplicons of the target nucleic acid and the novel oligonucleotide probe. PCR amplification begins by using a nucleic acid polymerase having 5' to 3' nuclease activity such that during the extension step of each PCR cycle, the nuclease activity of the polymerase allows cleavage and separation of the tag portion from the annealing portion of the tagged probe. The separated tag portion may optionally contain a modification (such as the non-nucleotide linker) such that it is not capable of being extended by a nucleic acid polymerase.

The separated tag portion is then hybridized with an oligonucleotide that is attached on a molography chip. The attached oligonucleotide is referred as a "moligo", and comprises two portions, an annealing portion comprising a nucleotide sequence complementary to the tag portion of the tagged probe, and an extension portion comprising a nucleotide sequence that is non-complementary to the target nucleic acid sequence or to the tag portion of the tagged probe. The moligo is acted as a template for the extension of the separated tag portion which serves as primer as it hybridizes with the annealing portion of the moligo and is extended along the extension portion of the moligo to form an extended duplex molecule. The generation of this extended duplex on the chip is then detected using focal molography.

Focal molography has been described recently as a novel analytical method for the detection of molecular interactions in biological samples (see Fattinger, C., *Physical Review X*, 4, 031024, 2014; Gatterdam, V. et al., *Nature Nanotechnology* 12, 1089-1095, 2017). Briefly, in focal molography, coherent laser light is diffracted at a coherent assembly of interaction sites. The coherent assembly comprises a precise submicrometer pattern of identical interaction sites that needs to be phase-matched to the incident coherent light over the entire pattern. The light diffracted at this assembly constructively interferes in a diffraction-limited focal spot (Airy disc). A molecular assembly with these properties is termed a "mologram". In essence, a mologram is a synthetic hologram composed of molecules, which scatters light into a diffraction-limited focal spot and is tuned such that it allows molecular interaction analysis. Acquisition of the molographic signal is realized through detection of the diffracted coherent light in the focus of the mologram. The light intensity in the molographic focus scales quadratically with the surface mass density modulation of the mologram. Background scattering by molecules that are randomly attached to the assay surface is intrinsically separated by focal molography from the coherent molographic signal. Molography does not require the presence of a label. Thus, label-free molography visualizes biomolecular recognition events through the detection of minute phase-contrast changes in the nanoenvironment of the recognition sites in the mologram. This opens up new perspectives and possibilities in analyzing non-covalent interactions.

In the measuring of biological interactions, most bioanalytical methods face severe problems with background signals or involve laborious referencing procedures. Although some methods such as fluorescence-based techniques (e.g. Forster resonance energy transfer or FRET) bypass some of these problems, they may disturb the studied molecular interactions as a result of the use of fluorescent dyes or other interfering labels. In contrast, focal molography transforms the invisible affinity modulation of the mologram into refractive index modulation, inducing a focused beam of light, where the affinity modulation is the difference in recognition site density for the target molecule between ridges and grooves. Discrimination between specific and non-specific binding is achieved by minimizing separation of the sensing and reference channel to its extreme—to less than the wavelength of light—while several hundreds of referencing and signal areas are embedded into a single sensing spot.

To perform a meaningful molographic measurement, a few instrumentation requirements need to be satisfied. Focal molography requires a suitable dark-field illumination of the mologram, which can be realized by the guided mode of a high-refractive-index thin-film optical waveguide. This assures a high signal-to-background ratio. Molography also needs a submicrometer-scale coherent pattern of recognition sites, which can be created by a variety of existing soft lithography methods that were developed for biochips. One particular embodiment involves the use of a photoactivatable graft copolymer, similar to the graft copolymers described by Serrano et al. (*Macromol. Rapid Commun.* 37, 622-629, 2016), to coat tantalum pentoxide ($Ta_2O_5$) thin-film optical waveguide. This copolymer has four key properties. (1) Before photolithographic exposure, the copolymer layer on the assay surface is monolithic and homogenous, both in terms of its chemical and optical properties. The monolithic layer does not contain coherently arranged molecules, so it shows no molographic signal before the photolithography step. (2) The copolymer layer is resistant to nonspecific molecular adsorption. While this copolymer layer exhibits defects and irregularities on the nanometer scale, these defects are not coherently arranged and do not contribute to the molographic signal. (3) The copolymer layer contains a photoactivatable functional group for formation of the recognition sites by exposure to light. (4) The formed copolymer adlayer allows necessary chemical and biochemical modifications after initial surface coating and is sufficiently stable to allow for temperature cycling during PCR reaction.

Embodiments of the present invention will be further described in the following examples, which do not limit the scope of the invention described in the claims.

EXAMPLES

Example 1 Feasibility Study: Cleavage and Extension of HIV-LTR Probe in Solution A real-time PCR experiment was performed to verify that a tagged probe comprising an annealing portion that is able to hybridize to a section of the HIV-1 LTR gene and a unique tag portion would be cleaved in the presence of the target HIV-1 LTR gene and that the released tag portion would be able to anneal to and extend off a "moligo" template that comprises a sequence that is complementary to the tag portion. The nucleotide sequences of the tagged probe and the moligo are shown in TABLE 1.

TABLE 1

| Name | Sequence | Modifications | SEQ ID NO: |
|---|---|---|---|
| HIV-1 LTR tag 3 probe | **F**CACACATTGGCA CCGCCGTCTTCTC TAGCAGTGGCGCC CGAACAGGGAC**p** | **F** = FAM **p** = phosphate; tag underlined | 1 |
| Moligo tag 3 | TTTTTTTTTTTTA GAGAAGACGGCGG TGCCAATGTGTG**p** | **p** = phosphate; complement to tag underlined | 2 |

Figure 2:
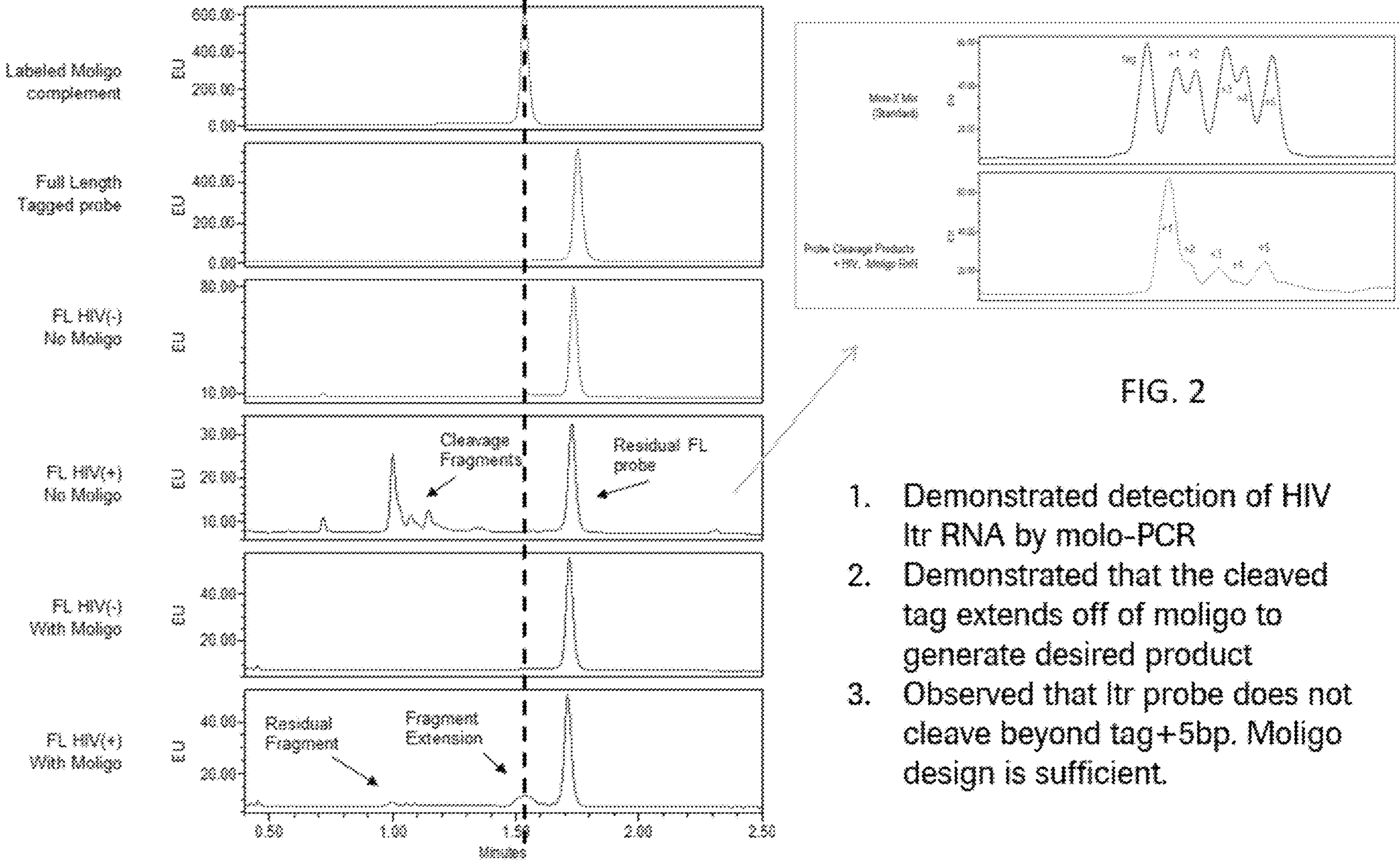
FIG. 2 shows the HPLC chromatographs from the PCR experiment performed as described in Example 1.

PCR assays were set up in individual wells in either presence (FL (HIV(+)) or absence (FL HIV(−)) of the target HIV-1 LTR gene and also in either the presence or absence of the Moligo tag 3 template. At the conclusion of the assays, aliquots from the wells were taken and subject to HPLC chromatography to analyze the resulting products. The results of the experiment are shown in the chromatographs on FIG. 2. In PCR reactions in the presence of the target gene, and absence of the tag 3 moligo, peaks representing cleavage fragments of the HIV-1 LTR tag probe were observed (see FL HIV(+) No Moligo graph). Closer examination of these cleavage product peaks revealed that they represented fragments containing the full tag portion with one (+1), two (+2), three (+3), four (+4) or five (+5) nucleotides from the annealing portion (see bottom right graph on FIG. 2). Interestingly, in reactions in the presence of both the target gene and the tag 3 moligo, (see FL (HIV(+) With Moligo graph) a small peak that corresponds in size with a full-length labeled Moligo complementary sequence was observed. This result demonstrated that the cleaved tag portion was able to hybridize to and extend off the moligo template in solution and provided feasibility of performing this type of assay on a moligo template that is immobilized on a solid phase.

Figure 3:
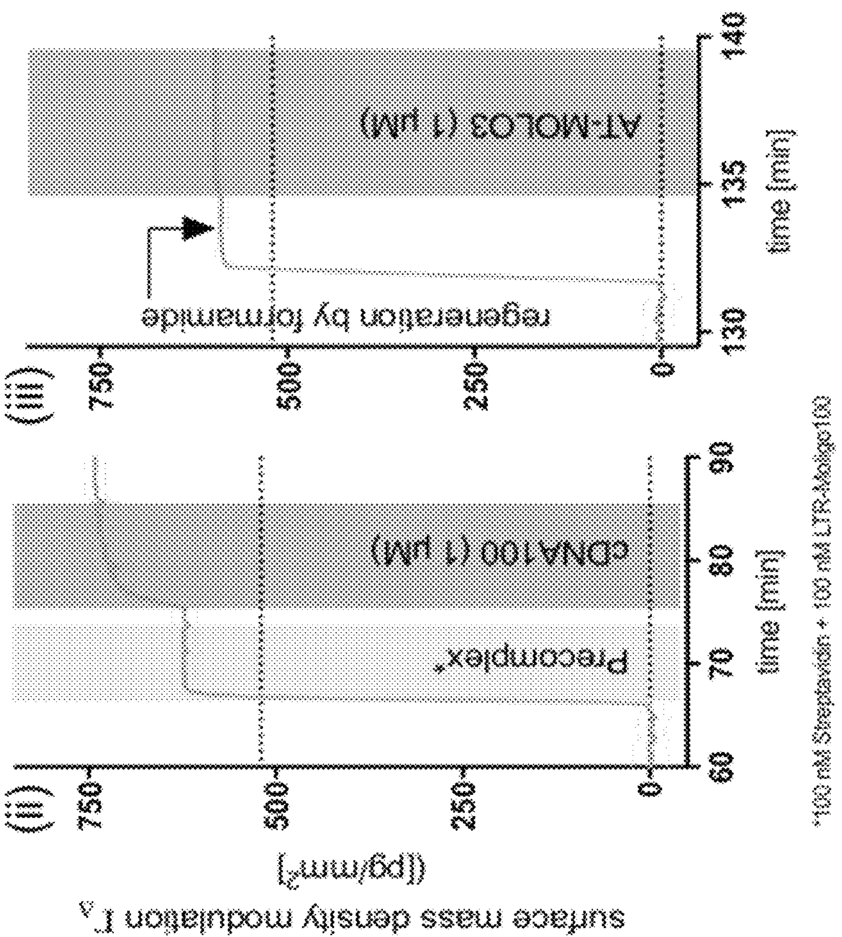
FIG. 3 shows the molography signals generated from the experiment described in Example 2.
Figure 3:
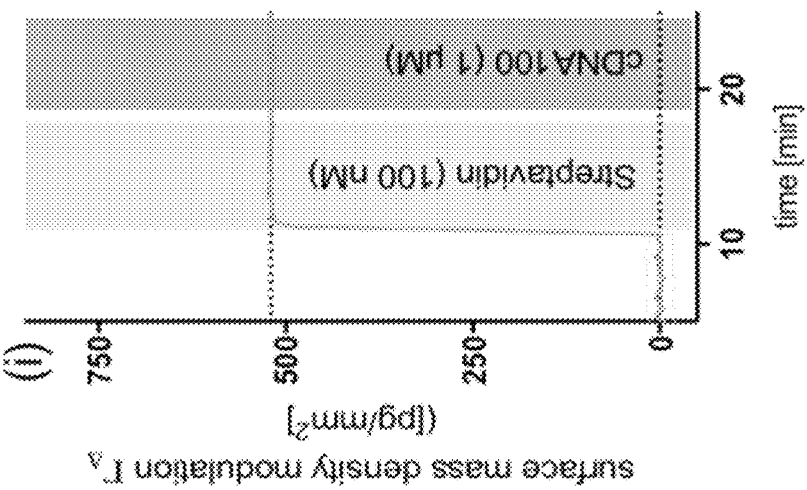
Figure 4:
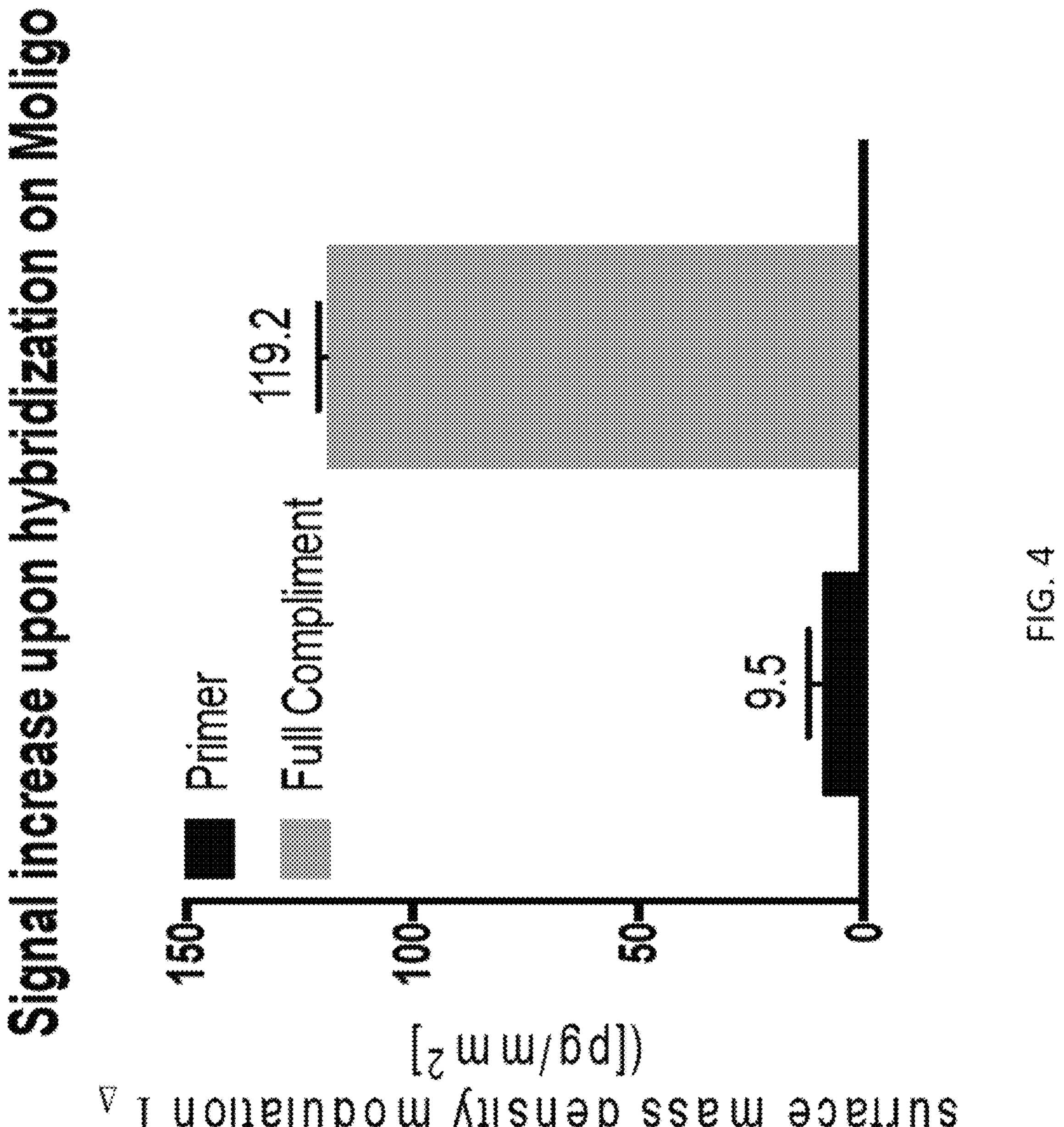
FIG. 4 shows a bar-graph representation of the molography signals between hybridization on the 100-bp moligo by an oligonucleotide consisting of a 22-bp primer sequence and by an oligonucleotide consisting of a 100-bp sequence complementary to the moligo sequence.

Example 2 Feasibility Study on Detection of Nucleic Acid Hybridization by Molography A feasibility study for the detection of nucleic acid hybridization and extension by molography was performed on the Zeptochip microarray chip (Zeptosens A G, Witterswil, Switzerland) which has been described in Pawlak M. et al., *Proteomics* 2002; 2(4): 383-93, which is incorporated herein by reference in its entirety. A running DNA-buffer consisting of 20 mM Tris, 5 mM $MgCl_2$, 50 mM KCl, pH 8.0 was applied to the flow chambers within the chip's flow-thru system at a constant flow rate of 15 µL/minute. First, Streptavidin (SAv) was injected as a normalization signal for focal molography to a surface mass density modulation of 520 pg/mm$^2$. A negative control between cDNA with no affinity tag and immobilized SAv generated no change in molographic signal (see FIG. 3 (*i*)) which represented no unwanted interaction having taken place. Next, immobilization of a biotin-tagged 100-bp HIV-LTR moligo oligonucleotide (SEQ ID NO: 4) was achieved with a 1:1 ratio of 100 nM SAv and biotinylated HIV-LTR moligo-100 as a precomplex. The formation of this precomplex resulted in an increase in molography signal as shown in the comparison between FIG. 3 (*i*) and FIG. 3 (ii) left side. Hybridization was then compared between the immobilized HIV-LTR moligo-100 and either a 22-bp primer, AT-MOLO-3 (SEQ ID NO: 3) which can bind to the annealing portion of the moligo-100 template (FIG. 3 (iii)) or a 100-bp sequence that is fully complementary to the moligo-100 template (FIG. 3 (ii) left side. The increase in the molographic signal between the hybridization of the 22-bp primer and the 100-bp complementary sequence is graphically represented in FIG. 4. This shows that molography is capable of distinguishing between a cleaved tag that is extended and one that is not extended.

```
INFORMAL SEQUENCE LISTING
SEQ ID NO 1:
HIV-1 LTR tag 3 probe sequence
CACACATTGGCACCGCCGTCTTCTCTAGCAGTGGCGCCCGAACAGGGAC
```

-continued

```
SEQ ID NO 2:
Moligo tag 3 oligonucleotide sequence
TTTTTTTTTTTTAGAGAAGACGGCGGTGCCAATGTGTG

SEQ ID NO 3:
AT-MOLO-3 oligonucleotide sequence
CACACATTGGCACCGCCGTCTT

SEQ ID NO 4:
HIV-LTR-moligo-100 oligonucleotide sequence
TTGCATGAGAATAGTAACGTATTGTGTAAAGCAGGATATAGAGTAATTGC

CCAGTTGTTCCAAATCGATATTGCAGAGAAGACGGCGGTGCCAATGTGTG
```

The invention claimed is:

1. A method for amplification and detection of a target nucleic acid in a sample comprising the steps of:

(a) contacting said sample containing said target nucleic acid in a single reaction vessel with (i) one pair of oligonucleotide primers, each oligonucleotide primer capable of hybridizing to opposite strands of a subsequence of said target nucleic acid;

(ii) a tagged probe comprising an oligonucleotide sequence that comprises an annealing portion and a tag portion, wherein the tag portion comprises a nucleotide sequence non-complementary to the target nucleic acid sequence, wherein the annealing portion comprises a nucleotide sequence at least partially complementary to the target nucleic acid sequence and hybridizes to a region of said subsequence of said target nucleic acid that is bounded by said pair of oligonucleotide primers;

(b) amplifying said target nucleic acid by PCR using a nucleic acid polymerase having 5' to 3' nuclease activity such that during an extension step of each PCR cycle, the nuclease activity of the polymerase allows cleavage and separation of the tag portion from the annealing portion of the tagged probe;

(c) hybridizing the cleaved tag portion from the tagged probe with a moligo template comprising an oligonucleotide sequence that comprises an annealing portion comprising a nucleotide sequence complementary to the tag portion of the tagged probe, and an extension portion comprising a nucleotide sequence that is non-complementary to the target nucleic acid sequence or to the tag portion of the tagged probe to form a partial duplex molecule, wherein said moligo template is attached on a solid phase chip;

(d) measuring formation of the partial duplex molecule in step (c) by molography;

(e) reacting the partial duplex molecule with a nucleic acid polymerase to extend the cleaved tag portion into the extension portion of the moligo template; and (f) measuring the extension in step (e) by molography, wherein an increase in a molographic signal between step (c) and step (e) represents detection of the presence of the target nucleic acid;

wherein all steps (a)-(f) are performed in the absence of a label.

2. The method of claim 1, wherein the length of the moligo template is longer than the length of the tagged probe by at least 10 nucleotides.

3. The method of claim 1, wherein the length of the moligo template is longer than the length of the tagged probe by at least 20 nucleotides.

4. The method of claim 1, wherein the length of the moligo template is longer than the length of the tagged probe by at least 30 nucleotides.

5. The method of claim 1, wherein the length of the moligo template is longer than the length of the tagged probe by at least 40 nucleotides.

6. The method of claim 1, wherein the length of the moligo template is longer than the length of the tagged probe by at least 50 nucleotides.

7. The method of claim 1, wherein the annealing portion and the tag portion of the tagged probe are separated by a non-nucleotide linker.

8. The method of claim 7, wherein the linker is a linear moiety or a cyclic moiety.

9. The method of claim 7, wherein the linker is derived from a single unit or from multiple identical or different units separated by phosphate linkages.

10. The method of claim 1, wherein the extension is detected using focal molography.

11. A method for amplification and detection of a target nucleic acid in a sample comprising the steps of:

(a) contacting said sample containing said target nucleic acid in a single reaction vessel with (i) one pair of oligonucleotide primers, each oligonucleotide primer capable of hybridizing to opposite strands of a subsequence of said target nucleic acid;

(ii) a tagged probe comprising an oligonucleotide sequence that comprises an annealing portion and a tag portion, wherein the tag portion comprises a nucleotide sequence non-complementary to the target nucleic acid sequence, wherein the annealing portion comprises a nucleotide sequence at least partially complementary to the target nucleic acid sequence and hybridizes to a region of said subsequence of said target nucleic acid that is bounded by said pair of oligonucleotide primers;

(b) amplifying said target nucleic acid by PCR using a nucleic acid polymerase having 5' to 3' nuclease activity such that during an extension step of each PCR cycle, the nuclease activity of the polymerase allows cleavage and separation of the tag portion from the annealing portion of the tagged probe;

(c) hybridizing the cleaved tag portion from the tagged probe with a moligo template comprising an oligonucleotide sequence that comprises an annealing portion comprising a nucleotide sequence complementary to the tag portion of the tagged probe, and an extension portion comprising a nucleotide sequence that is non-complementary to the target nucleic acid sequence or to the tag portion of the tagged probe to form a partial duplex molecule, wherein said moligo template is attached on a solid phase chip;

(d) reacting the partial duplex molecule with a nucleic acid polymerase to extend the cleaved tag portion into the extension portion of the moligo template; and (e) measuring the extension in step (d) by molography wherein an increase in a molographic signal between step (c) and step (d) represents detection of the presence of the target nucleic acid, wherein the tagged probe comprises SEQ ID NO: 1 and the moligo template comprises SEQ ID NO: 4.

* * * * *